United States Patent [19]

Priddy

[11] 4,288,379
[45] Sep. 8, 1981

[54] HYDROCARBON POLYL GEM-BIS(T-ALKYLPEROXY)ALKANOATES DERIVED FROM β-KETO-ACIDS

[75] Inventor: Duane B. Priddy, Coleman, Mich.

[73] Assignee: The Dow Chemical Company, Midland, Mich.

[21] Appl. No.: 802,216

[22] Filed: May 31, 1977

[51] Int. Cl.$^3$ .................................... C07C 179/06
[52] U.S. Cl. .................. 260/410.6; 260/410.7; 560/129; 252/426
[58] Field of Search ................... 560/129, 186; 260/610 R, 610 C, 410.6, 410.7

[56] References Cited

U.S. PATENT DOCUMENTS

| | | | |
|---|---|---|---|
| 2,455,569 | 12/1948 | Dickey | 260/610 C |
| 3,630,960 | 12/1971 | Chetakian | 252/426 |
| 3,649,546 | 3/1972 | McCloskey et al. | 252/186 |
| 3,964,950 | 6/1976 | Boles | 156/331 |
| 4,052,464 | 10/1977 | Priddy | 260/610 R |

OTHER PUBLICATIONS

Kirk-Othmer "Enc. of Chem. Tech." 2nd Ed. vol. 1, pp. 153 and 158.
Hattori, Seiji et al. "Peroxyketals" Japan Kokai 74,110,617 dated Oct. 22, 1974, (See Chemical Abstracts vol. 82 (1975) #155,350f).
Pennwalt-Lucidol Preliminary Data Sheet, Product Bulletin R-233, No date.
Witco Chemical US Peroxy Division, Technical Bulletin USP-333, No date.
Cubbon, R.C.P. et al. "Organic Peroxides Containing Functional Groups" Pts. II and III, J. Chem. Soc. (1968) pp. 2983-2988.

Primary Examiner—Natalie Trousof
Assistant Examiner—L. Hendriksen
Attorney, Agent, or Firm—Charles J. Enright

[57] ABSTRACT

The title compounds are useful vinyl polymerization initiators of high thermal stability and correspond to the formula:

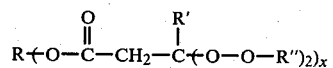

wherein R is an x-valent hydrocarbon whose chain length can be interrupted by one or more ether linkages, R' is an aliphatic moiety of 1 to about 10 carbon atoms, R" is a tertiary hydrocarbon, and x is an integer of at least 2.

8 Claims, No Drawings

HYDROCARBON POLYL GEM-BIS(T-ALKYLPEROXY)ALKANOATES DERIVED FROM β-KETO-ACIDS

BACKGROUND OF THE INVENTION

1. Field of the Invention

This invention relates to a novel class of high temperature, polyfunctional initiators and a process for their preparation.

2. Description of the Prior Art

Polyfunctional peroxides are known initiators for the polymerization of vinyl monomers and the cross-linking of various polymers. However, few of these initiators have tetra or higher peroxide functionality, and of those that do, none have a one hour temperature half-life greater than about 130° C.

SUMMARY OF THE INVENTION

Hydrocarbon polyl gem-bis(t-alkylperoxy) alkanoates are provided which correspond to the formula:

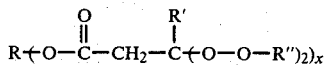

wherein R is an x-valent hydrocarbon whose chain length can be interrupted by one or more ether linkages, R' is an aliphatic moiety of 1 to about 10 carbon atoms, R" is a tertiary hydrocarbon, and x is an integer of at least 2, and preferably 2, 3, or 4. These compounds are useful as initiators in the preparation of addition polymers of vinyl monomers, such as styrene, acrylonitrile, butadiene, alpha-methylstyrene, and the like. These compounds also represent an advance over the prior art in that they have a higher thermal stability (at least about 130° C.) than previously known polyfunctional initiators.

DESCRIPTION OF THE INVENTION

"Hydrocarbon polyl" refers to the alcohol portion (R) of the molecule and includes alkanes and arenes substituted with side chains, ether linkages, and cyclic groups. The "-polyl" means that a plurality of the alkanoate functionalities are attached to said alcohol portion. "Alkanoates" refers to the acid portions of the molecule which have been esterified with a polyhydric alcohol. The acid portions of the molecule may also contain side chains.

The polyfunctional initiators of the present invention have a one-hour half-life of at least about 130° C., and generally between about 130° and about 140° C. As a consequence, these initiators permit the polymerization of vinyl monomers at higher temperatures than heretofore practical. This results in a faster polymerization rate but without sacrificing the high average molecular weight and broad molecular weight distribution which are characteristic of polyfunctional peroxide initiators. These compounds can also be used singly or in admixture with one another to initiate polymerization.

The present compounds are employed in substantially the same manner as previously known peroxide initiators, adjusting the weight percent used to compensate for the typically higher molecular weight of the present initiators. Polyfunctional initiators are typically employed in amounts of at least about 0.6 milliequivalents per liter (meq/l) of substrate (material to be polymerized or cross-linked), and preferably of at least about 1 meq/l. Practical considerations, such as economy and convenience, are the only limitations upon the maximum amount of initiator that can be used but a typical maximum amount is about 12 and preferably about 3.7 meq/l.

Polymerizations are initiated by the instant compounds when the temperature of a mixture of them with the vinyl monomers is at least about 120° C. These initiators are useful at temperatures of as high as about 160° C., and are preferably used at temperatures of about 130° C.–160° C. In a preferred mode of practice, the present initiators are used sequentially with lower temperature initiators. By this method, vinyl monomers are, for example, heated to about 100° C., at which temperature some other initiator starts polymerization. After a suitable period, the mixture is further heated to a higher temperature, e.g., 130° C.–135° C., at which a substantial portion of these peroxide initiators will decompose to the free radical form and thus initiate further polymerization.

The instant initiators are also suitable for use in initiating cross-linking of polymers containing vinyl unsaturation, particularly in vulcanizing rubber and in the curing of polyester with styrene.

These hydrocarbon polyl peroxy alkanoates can be produced from the corresponding ketone, i.e.,

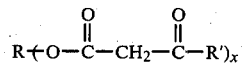

by contacting (reacting) the ketone with a tertiary hydroperoxide, in an amount at least sufficient to react with the ketone. An excess of hydroperoxide results normally in a high conversion of the ketone. It is therefore desirable to employ between about one and one-half and about four times the theoretical amount of tertiary hydroperoxide needed. The reaction between the hydroperoxide and the ketone requires the presence of an acid catalyst, such as p-toluenesulfonic acid, sulfuric acid, phosphoric acid, acidic ionic exchange resins, acidic clay, etc. All known acidic catalysts which promote the addition of tertiary hydroperoxide to a ketone to form the corresponding diperoxyketal can be employed. Water is normally removed from the mixture as it is formed, by distillation of a water-solvent azeotrope at reduced pressure. The contacting is conducted at a temperature of at least about 30° C. and preferably of at least about 40° C. For reasons of product degradation and reaction control, the maximum temperature is generally about 80° C. and preferably about 65° C. After allowing a suitable time for reaction to occur, e.g. one hour, the mixture may optionally be intimately contacted with a suitable reagent to neutralize the acid catalyst, such as sodium acetate, and then agitated vigorously for a suitable period, e.g. several minutes. This optional step ensures that the acid catalyzed reaction has ceased. The reaction produces a slurry, from which the desired product can be separated, as by filtration and evaporation under a stream of nitrogen.

The ketones are known compounds, which can be produced, for example, by intimately contacting a suitable lactone and a suitable polyhydric alcohol in stoichiometric quantities in the presence of an appropriate acid catalyst, such as p-toluenesulfonic acid, sulfuric acid, phosphoric acid, acidic ionic exchange resin, acidic clays, and the like. Suitable lactones include those in which the carbon atom alpha to the ring oxygen is connected by a double bond to a carbon atom outside the ring, as:

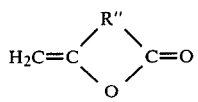

However, the ring cannot be larger than four members. It is not intended that the carbonyl carbon be included in the description "alpha to the ring oxygen." The lactone-alcohol reaction may be accomplished, for example, using a solution of the reactants in ethyl benzene and heating at reflux for a suitable time, e.g., one hour. The ketones may be formed either separate or in situ, but in situ preparation is preferred as it is generally more convenient, eliminating, for example, intermediate purification of the ketone. With in situ preparation, it is convenient to use the same catalyst in producing the ketone as in producing the final product (hydrocarbon polyl peroxy alkanoates).

In the formula for the novel compounds of the present invention, R may be referred to as the "alcohol portion" of the molecule, since in the usual method of producing the ketone, this portion is derived from the original alcohol. The structure of R thus is that of a dehydroxylated polyhydric alcohol. The peroxy-substituted acid functionalities are bonded to this group in place of the absent hydroxy groups. The alcohol portion of the compound can be varied to convenience. However, the alcohol portion preferably contains not more than about 5 ether linkages and/or not more than a total of about 30 carbon atoms, as a larger alcohol portion increases the equivalent weight and thereby effectively reduces the concentration of peroxide functionality. Apart from this limitation, the chief constraint on the structure of the alcohol portion is the cost and availability of the alcohol from which it is derived. Because of this constraint, it is preferred that diols which do not contain an ether linkage and monomers of the polymeric forms each contain no more than about 6 carbon atoms. The number of hydroxy groups on the alcohol determines the number of peroxy moieties which will be present in the hydrocarbon polyl alkanoate. While the alcohol can contain any number of hydroxyl groups, little additional advantage is gained by using an alcohol with more than four as such alcohols are not readily available. Pentaerythritol is an example of a suitable alcohol with four hydroxyl groups.

Glycerol or other triols can be employed to form the alcohol portion, giving a compound containing six peroxy groups and three ester linkages. Additionally, polymeric forms of glycerol, such as for example, triethers of glycerine with polyalkylene oxides containing terminal hydroxyl groups, can also be used.

Diols which can be used to form the alcohol portion are preferably lower ($C_2$–$C_6$) primary and secondary alkyl diols, as for example ethylene glycol, 1,6-hexanediol, and the like, and polymeric forms thereof, as for example, diethylene glycol, triethylene glycol, and the like. Arene diols, and especially benzene diols, are also suitable, such as, for example, bisphenol A, resorcinol, and hydroquinone. The aliphatic portion(s) of the diol may be either straight chain, as for example, in propylene glycol or dipropylene glycol, or branched as, for example, in butylene glycol, dibutylene glycol and the like. It is also possible to use mixed polymers, such as for example:

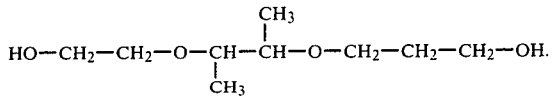

Because of cost, the simpler diols are preferred, particularly ethylene glycol, propylene glycol, and polymeric forms of these with up to about four monomer units.

The aliphatic moiety (R') of 1 to 10 carbon atoms is either straight- or branched-chain or cyclic. Illustrative moieties include: Methyl, ethyl, propyl, isopropyl, octyl, decyl, neopentyl, cyclohexyl, etc. Preferably, R' is a straight-chain aliphatic moiety of 1 to 4 carbon atoms and most preferably methyl or ethyl. When R' is methyl or ethyl, the alkanoate is, of course, butyrate or valerate, respectively.

The particular tertiary group (R") used in the peroxide moieties can also be varied to convenience. Cyclic or other substituted tertiary alkyls, such as t-cumyl, or t-amyl moieties can be employed. Especially preferable is t-butyl, because t-butyl hydroperoxide is slightly more reactive in the formation of the product than are other tertiary hydroperoxides, and it is much less expensive.

Representative hydrocarbon polyl gem-bis-(t-alkylperoxy)alkanoates include: Alkane- and arenediols, such as 1,3-propane-, 1,4-butane- and 1,6-hexanediol bis[3,3-bis(t-butylperoxy)butyrate], bisphenol A, resorcinol and hydroquinone bis[3,3-bis(t-amylperoxy)valerate], etc.; glycerols, such as glycerol tris[3,3-bis(t-butylperoxy)butyrate], glycerol tris[3,3-bis(t-cumylperoxy)butyrate], etc.; polymers of alkane- and arenediols, such as propylene, dipropylene and tripropylene glycol bis[3,3-bis(t-butylperoxy)butyrate], 3,3'-oxydiphenol bis[3,3-bis(t-butylperoxy)valerate], etc.; copolymers of alkane- and arenediols, such as ethylenepropylene glycol bis[3,3-bis(t-butylperoxy)butyrate]; 3,4'-oxydiphenol bis[3,3-bis(t-butylperoxy)butyrate]; p-hydroxyethyleneoxyphenol bis[3,3-bis(t-butylperoxy)butyrate], etc.; and pentaerythritols, such as pentaerythritol tetra[3,3-bis(t-butylperoxy)butyrate]; pentaerythritol tetra[3,3-bis(t-cumylperoxy)valerate], etc.

The following examples are illustrative of certain, specific embodiments of this invention.

SPECIFIC EMBODIMENTS

Example 1

Diketene (8.4 g), diethylene glycol (5.3 g), ethyl benzene (50 ml) and p-toluenesulfonic acid (30 mg) were heated at reflux for one hour. The temperature of the reaction was about 140° C. t-Butyl hydroperoxide (54 g) was then added, followed by another 100 mg of p-toluenesulfonic acid. The pressure in the reaction vessel was then reduced to from 20 to 100 mm of mercury, in order to distill water from the mixture while maintaining the reaction temperature at from 40° C. to about 50° C. After about one hour, sodium acetate (1 g) was added and the resulting mixture stirred vigorously for 10 minutes. A slurry resulted, which was filtered and evaporated under a stream of nitrogen to yield 23.4 g of light yellow oil. Nuclear Magnetic Resonance analysis of this oil in perchloroethylene showed that the desired product, diethylene glycol bis[3,3-bis(t-butylperoxy)butyrate], was formed. The one-hour half-life of this compound is 135° C.

Example 2

A. Diketene (16.8 g) and ethylene glycol (6.2 g) were stirred together in benzene (50 ml) while concentrated HCl (5 drops) was added. The resulting mixture was warmed to about 50° C. and there maintained for about 2 hours. The mixture was then cooled to ambient temperature and added to a mixture of t-butyl hydroperoxide (54 g), benzene (50 ml) and anhydrous calcium chloride (50 g). This resulting mixture was agitated at ambient temperature while additional concentrated HCl (5 drops) was added. An exotherm raised the temperature to about 35° C. and agitation continued for about 1 hour. The mixture was then filtered and evaporated under a stream of nitrogen to yield an oil, ethylene glycol bis(t-butylperoxy)butyrate.

B. The oil (0.05 g) prepared in (A) was dissolved in styrene (100 g) and the resulting styrene solution was placed in a glass ampoule and sealed under nitrogen. A second ampoule was filled with styrene without the oil and also sealed under nitrogen. Both ampoules were then placed in an oil bath at about 125° C. After 1 hour the ampoules were removed and analysis showed that the ampoule without the oil contained about 14 percent polystyrene while the ampoule with the oil contained about 25 percent polystyrene.

Although this invention has been described in considerable detail by the preceding examples, it is to be understood that such detail is for purposes of illustration only and is not to be construed as limitations upon the invention. Many variations can be had upon the preceding examples without departing from the spirit and scope of the appended claims.

What is claimed is:

1. A hydrocarbon polyl gem-bis(t-alkylperoxy)alkanoate which has a one-hour half-life of at least about 130° C. and corresponds to the formula:

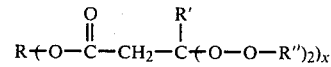

wherein R is an x-valent hydrocarbon whose chain length may be interrupted by one or more ether linkages;

R' is an aliphatic moiety of 1 to about 10 carbon atoms;

R" is a tertiary hydrocarbon; and x is an integer of at least 2.

2. The hydrocarbon polyl gem-bis(t-alkylperoxy)alkanoate of claim 1 wherein x is 2, 3 or 4.

3. The hydrocarbon polyl gem-bis(t-alkylperoxy)alkanoate of claim 2 wherein R' is a straight-chain aliphatic moiety of 1 to 4 carbon atoms.

4. The hydrocarbon polyl gem-bis(t-alkylperoxy)alkanoate of claim 3 wherein the alcohol from which the structure of R is derived is selected from the group consisting of:

(a) primary or secondary alkane diols containing from 2 to about 6 carbon atoms;

(b) glycerol;

(c) polymers of any of the alcohols in (a) or (b) which contain a total of from 4 to about 30 carbon atoms;

(d) copolymers of 2 or more of the alcohols in (a) and (b) which contain a total of from 4 to about 30 carbon atoms; and (e) pentaerythritol.

5. The hydrocarbon polyl gem-bis(t-alkylperoxy)alkanoate of claim 4 wherein x is 2.

6. The hydrocarbon polyl gem-bis(t-alkylperoxy)alkanoate of claim 5 wherein R' is methyl or ethyl.

7. The hydrocarbon polyl gem-bis(t-alkylperoxy)alkanoate of claim 6 wherein said alcohol is diethylene glycol.

8. The hydrocarbon polyl gem-bis(t-alkylperoxy)alkanoate of claim 7 wherein R" is t-butyl.

* * * * *